United States Patent [19]

Bass, Jr.

[11] Patent Number: 5,107,825
[45] Date of Patent: Apr. 28, 1992

[54] ADJUSTABLE RESILIENT PAD FOR SUPPORTING A PATIENT'S EXTREMITY MOUNTED WITH AN EXTERNAL FIXATOR

[76] Inventor: William E. Bass, Jr., 689 Oak Ridge Dr., Union, Ky. 41091-9666

[21] Appl. No.: 515,561

[22] Filed: Apr. 27, 1990

[51] Int. Cl.⁵ .............................................. A47C 20/00
[52] U.S. Cl. .......................................... 602/24; 5/461; 5/652; 602/26
[58] Field of Search ................. 606/53, 54; 128/80 A, 128/80 R, 80 C; 5/443, 431, 432, 440, 437, 436

[56] References Cited

U.S. PATENT DOCUMENTS

| | | | |
|---|---|---|---|
| 3,946,451 | 3/1976 | Spann | 5/443 |
| 3,995,846 | 12/1976 | Frick | 5/443 |
| 4,186,738 | 2/1980 | Schleicher et al. | 128/80 R |
| 4,392,489 | 7/1983 | Wagner, Sr. | 128/80 A |
| 4,471,952 | 9/1984 | Spann | 5/443 X |
| 4,779,296 | 10/1988 | Bond | 5/443 X |
| 4,805,605 | 2/1989 | Glassman | 128/80 A |
| 4,886,258 | 12/1989 | Scott | 128/80 R X |
| 4,927,139 | 5/1990 | Taltre | 5/431 |

OTHER PUBLICATIONS

Green, Stuart A. MD, Ilizarov Orthopedic Methods, AORN Journal, Jan. 1989, vol. 49, No. 1.

Primary Examiner—Robert A. Hafer
Assistant Examiner—Kerry Owens
Attorney, Agent, or Firm—Wood, Herron & Evans

[57] ABSTRACT

An adjustable resilient pad is disclosed that is used in conjunction with an orthopedic external fixator as means for supporting a patient's extremity during therapeutic treatment.

9 Claims, 1 Drawing Sheet

ADJUSTABLE RESILIENT PAD FOR SUPPORTING A PATIENT'S EXTREMITY MOUNTED WITH AN EXTERNAL FIXATOR

FIELD OF THE INVENTION

This invention relates to resilient pads as means for support, and more particularly to a supporting resilient pad used in conjunction with an external fixator for a patient's extremity.

BACKGROUND OF THE INVENTION

Innovations in orthopedic surgical techniques have brought about the use of external fixators to combat bone deformities and deficiencies associated with patient's limbs. External fixators function as devices for the lengthening of abnormal bones caused by genetic dispositions, diseases, and accidents. The devices operate by encircling the circumference of the patient's limb with orthopedic rings. The rings are secured by therapeutic pins that impale the limb and outer support rods that connect the rings and increase tension. Moreover, the device's adjustability lies in the mobility of the rings. Adjustability is the important factor in correcting abnormalities in bone structure. However, the apparatus, although adaptable to suit a patient's proportions and deformities, can be cumbersome when the patient lies in the prone or supine position. This can cause undue stress in the limb and an additional amount of pain and discomfort to the patient.

With the advent of adaptable fixating devices, means for supporting the patient's body was needed. In the Soviet Union where external fixation or the Ilizarov Orthopedic Method was introduced approximately thirty-five years ago, support techniques were formulated. For instance, a special mattress was constructed which enabled a patient with a fixator apparatus attached posterior to the buttock to lie in the supine position. The mattress contained a hole which allowed the fixed apparatus to sink into the hole at the level of the patient's buttock.

There is a definite need to develop new means for administering treatment with external fixators and alleviating patients, discomfort.

SUMMARY OF THE INVENTION

In a broad aspect of the present invention, a resilient pad is provided that enables a patient to be comfortably supported when a treated extremity is mounted with an external fixating device.

In a more specific aspect of the invention, the resilient pad has at least one perforated removable section for forming a pocket to receive the external fixator therethrough. The pad has sufficient length for resiliently supporting a limb on a side of the pocket so that a patient's limb rests comfortably while the limb mounted fixator sits in the pocket for support by an underlying support surface such as a mattress.

In one embodiment, the pad is adapted for placement on top of a mattress bed and box spring that supports the patient. The pad is formed of a body of foam throughout, preferably an open cell foam for better air circulation around the body. The foam has sufficient density that allows for resilient and comfortable support of the treated limb while the fixator rests on the underlying surface.

In another embodiment in accordance with the features of the present invention, the pad is provided with a plurality of perforated removable portions or sections which vary in size. This feature of the invention allows different fixators of varying size to be used depending on the therapeutic treatment of a particular limb. Thus, in this form, a plurality of slits are formed at intervals along the pad length and one or more sections can be removed from the pad to form a pocket whose length or size will suit the device and limb. The thickness of the pad may vary to accommodate the treated limb comfortably. The slits are formed substantially through the resilient foam for ease of removal to form the pocket. Again, the length of the pad will vary to receive the external fixator so that the limb is supported on at least one side or both sides of the pocket.

In a further embodiment, the removable sections lying within the resilient pad are preferably defined by a plurality of slits formed substantially through the foam which outline the formation of the pocket. The slits vary in width to allow for smaller or larger portions to be removed as needed, even by hand without tools by tearing. Also a knife or scissors may be used to assist in complete removal. Further, the resilient pad is adaptable to support both the left and right extremities. By simply flipping the pad, it becomes appropriately useful for both the left and right bodily limbs. The pad is most adaptable for femoral and tibial fixators.

The above features and advantages of the present invention will be better understood with reference to the accompanying figures and detailed description. It is to be understood that the particular pad structure illustrating the invention is exemplary only and not to be regarded to be a limitation of the invention.

BRIEF DESCRIPTION OF THE DRAWINGS

Reference is made to the accompanying figures in which show illustrative embodiments of the present invention from which its novel features and functions will be apparent.

DETAILED DESCRIPTION OF THE PREFERRED EMBODIMENT

By way of illustrating a more complete appreciation and thorough understanding of the present invention and the advantages thereof, the following detailed description is given concerning the novel resilient pad and its functions with reference to the drawings.

Figure 1:
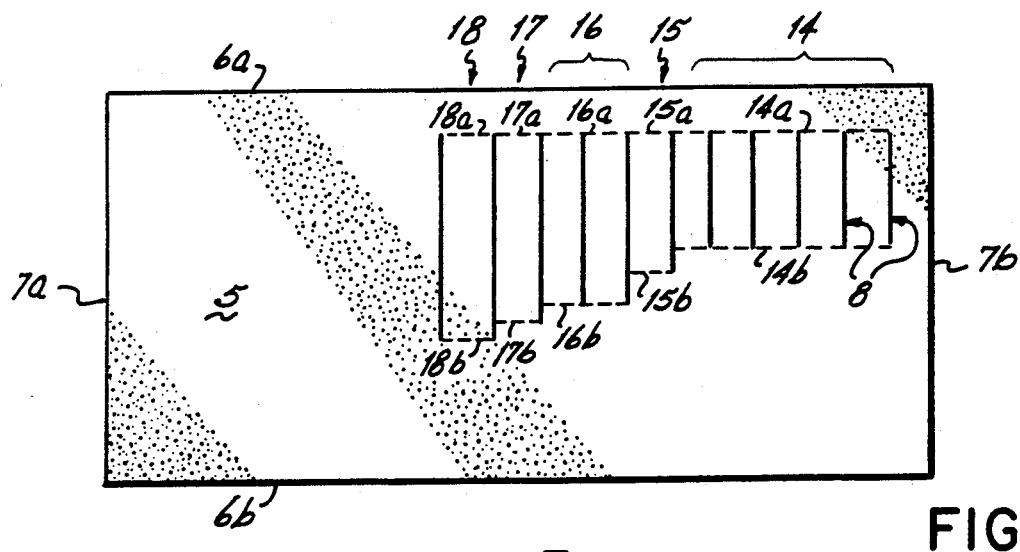
FIG. 1 is a plan view of a resilient foam pad structure of the present invention which illustrates a plurality of slits defining a plurality of perforated removable sections in the structure.
Figure 2:
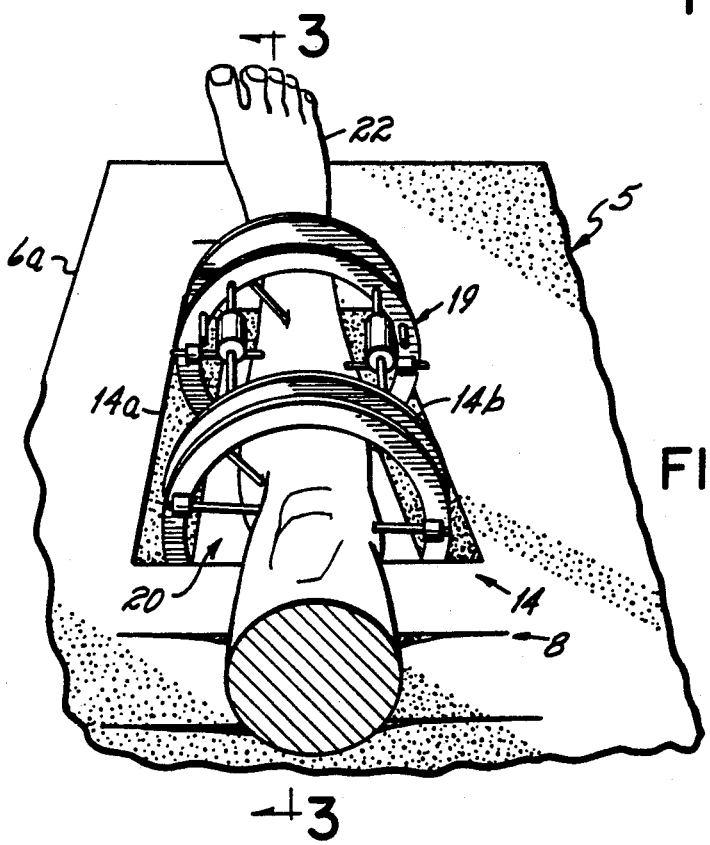
FIG. 2 is a perspective view of a part of the foam structure of FIG. 1 in use where sections have been removed to form a pocket that receives the external apparatus fixed on a limb.
Figure 3:
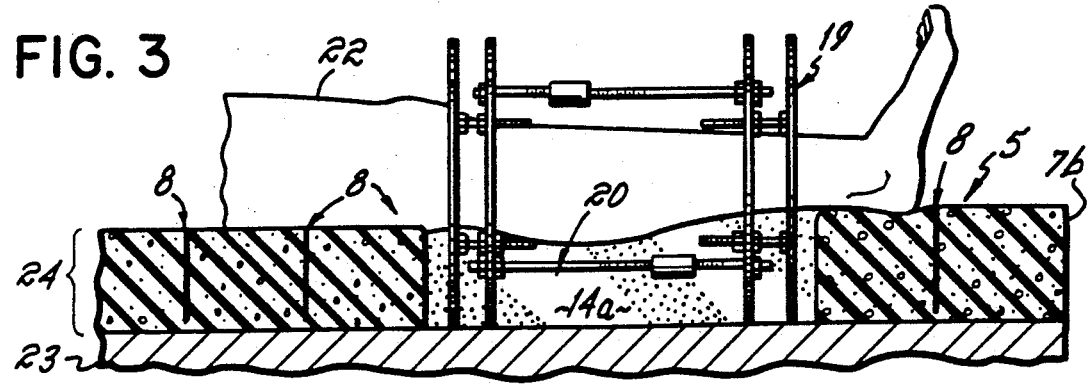
FIG. 3 is a cross-sectional view taken along line 3—3 of FIG. 2 which illustrates the foam pad structure having both sides of the pocket supporting the limb and the external apparatus resting on a mattress surface.

A pad 5 is shown in FIGS. 1-3 as a four-sided body of foam that is adapted to rest upon a mattress 23 for use with a leg fixator 19. The pad 5 has opposing sides 6a, 6b of equal length and width 7a, 7b and about 2.5 inches thickness. Dimensions of pad 5 are similar to the dimensions of a twin mattress or hospital bed allowing for it to rest upon a mattress bed for additional support.

Lying within the pad 5 shown in FIG. 1 is a plurality of slits 8 defining removable sections. The slits 8, eleven in all, outline a series of ten perforated sections which are removable. The slits 8 and, thus, the sections differ in width to accommodate the various sizes and placement of the adjustable external fixators. The ten perforated sections outlined by the eleven slits subdivide the foam pad 5 into a series of five portions.

The first portion 14 consists of five 9-inch wide slits and their corresponding sections. The slits 8 are in a parallel series four inches from the side 7b of the pad 5 and they penetrate substantially or completely through the pad 5. Thus, each section is a removable block of foam by tearing along sides 14a, 14b. If desired additional slits may be made along sides 14a, 14b for ease of removal. The series of 9-inch slits also lies four inches from one side 6a, 6b of the pad 5. The pad 5 shown is thirty-five inches wide so that the other end of the series of 9-inch slits falls twenty-two inches from the opposing side 6a, 6b. The five 9-inch slits also are separated from each other by a distance of four inches.

A second portion 15 consists of one 10-inch slit following the five previous 9-inch slits by a distance of four inches. Like the 9-inch slits, the 10-inch slit is also parallel with the sides 7a, 7b and penetrates substantially or completely through the pad 5. Thus, the corresponding section is a removable block of foam by tearing along sides 15a, 15b. The 10-inch slit lies four inches from the side 6a and is twenty-one inches from the opposing side 6b.

The third portion 16 comprises two 11-inch wide slits which follow the previous series of slits. The 11-inch slits also are parallel with the sides 7a, 7b of the pad 5 and lie four inches from the side 6a. The eleven-inch slits fall twenty inches from the opposing side 6b and penetrate substantially or completely through the pad 5 thereby allowing each section to be a removable block of foam by tearing along sides 16a, 16b.

The fourth portion 17 consists of one 12-inch wide slit and follows four inches from the previous portion 16 parallel with the sides 7a, 7b of the pad 5 and in line with preceding portions 14, 15, and 16 four inches from side 6a and nineteen inches from the other side 6b. Also, the 12-inch slit penetrates substantially or completely through the pad 5. Thus, the corresponding section is a removable block of foam by tearing along sides 17a, 17b.

The fifth portion 18 consists of one 13-inch slit four inches from side 6a and eighteen inches from opposing side 6b. The fifth portion 18 follows the same geometrical plane as the previous portions 14, 15, 16, and 17. It is parallel with the sides 7a, 7b of the pad 5. The final slit of portion 18 is a distance of thirty inches from the top 7a of the pad 5 and penetrates substantially through the pad 5 allowing for its corresponding section to be a removable block of foam by tearing along lines 18a, 18b.

The total distance between the eleven slits 8 which encompass the removable sections is forty inches. Each removable section is four inches in length. The remaining thirty-four inches of the length of the pad 5 is encompassed by a 30-inch distance from the 13-inch slit of portion 18 to the top 7a of the pad 5 and the 4-inch distance from the first 9-inch slit to the bottom 7b of the pad 5. With reference to FIG. 3, the thickness 24 of the resilient pad 5 is about 2.5 inches. The length and the width of the pad 5 shown in FIG. 1 is seventy-four inches and thirty-five inches, respectively.

Referring to FIG. 2 of the accompanying drawings, a part of the resilient pad 5 is shown in use with the external fixator 19 being received within a pocket 20 formed from the removal of a plurality of portions 14, for instance, by tearing or cutting the remainder of the foam. A limb 22 mounted with the external fixator 19 is shown resting on both sides of the pocket 20.

The features of FIG. 2 are more readily apparent in FIG. 3 which illustrates a cross-sectional view of FIG. 2 taken generally along line 3—3 of FIG. 2.

Shown in FIG. 3 is the pad 5 resiliently supporting the limb 22 on both sides of pocket 20. In accordance with features of the preferred embodiment, external fixator 19 is received by pocket 20 through the pad 5 and rests on the underlying support surface 23 directly. The resilient foam pad 5 has a sufficient density that enables resilient support for limb 22 mounted with the external fixating apparatus 19. An open cell polyurethane foam having a density of about 1.9 is satisfactory for example.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation and material to teachings of the invention without departing from the central scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A device for comfortably supporting a patient's limb that has an external fixator mounted thereon comprising:

a resilient pad having a plurality of removably sections defined by perforations in said pad whereby pocket means in said pad is formed upon removal of at least one removable section, said pad adapted to rest upon an underlying support surface, said pocket means for receiving an external fixator therethrough to rest upon said underlying support surface, said pad having a sufficient length for resiliently supporting the limb on at least one side of said pocket means when said pad rests upon the support surface.

2. The device of claim 1 with said pad adapted to rest upon a supporting mattress surface.

3. The device of claim 1 wherein said pocket means accommodates external fixators of varying dimension.

4. The device of claim 1 comprising a layer of foam having a plurality of slits to form said removable section.

5. The device of claim 4 having open cell foam structure for supporting said limb.

6. The device of claim 4 where said slits are formed at intervals along a length of said pad to form at least two removable sections.

7. A device for comfortably supporting a patient's limb that has an external fixator mounted thereon comprising:

a resilient pad formed from a body of foam throughout having a plurality of slits at intervals along the length of said pad defining at least two removable sections which form pocket means in said pad when removed, said pad adapted to rest upon an underlying support surface, said pocket means for receiving the external fixator therethrough to rest upon the support surface, the pad having a sufficient length for resiliently supporting the limb on at least one side of said pocket means when the pad rests upon the support surface.

8. The device of claim 7 with said resilient pad having open cell foam structure for supporting said limb.

9. The device of claim 7 with said supporting service comprising mattresses.

* * * * *